United States Patent
Bewley

(10) Patent No.: US 7,276,227 B2
(45) Date of Patent: Oct. 2, 2007

(54) OBLIGATE DOMAIN-SWAPPED DIMER OF CYANOVIRIN WITH ENHANCED ANTI-VIRAL ACTIVITY

(75) Inventor: Carole A. Bewley, Bethesda, MD (US)

(73) Assignee: United States of America, repesented by the Secretary, Department of Health and Human Services, Washington, DC (US)

( * ) Notice: Subject to any disclaimer, the term of this patent is extended or adjusted under 35 U.S.C. 154(b) by 70 days.

(21) Appl. No.: 10/505,666

(22) PCT Filed: Feb. 25, 2003

(86) PCT No.: PCT/US03/06115

§ 371 (c)(1),
(2), (4) Date: Dec. 8, 2004

(87) PCT Pub. No.: WO03/072594

PCT Pub. Date: Sep. 4, 2003

(65) Prior Publication Data

US 2005/0090643 A1    Apr. 28, 2005

Related U.S. Application Data

(60) Provisional application No. 60/359,360, filed on Feb. 25, 2002.

(51) Int. Cl.
*A61K 49/00* (2006.01)
*C07K 1/00* (2006.01)
*C12P 21/06* (2006.01)

(52) U.S. Cl. .................... 424/9.1; 435/69.1; 530/350

(58) Field of Classification Search ................ 435/7.8; 530/350
See application file for complete search history.

(56) References Cited

U.S. PATENT DOCUMENTS 5,821,081 A   10/1998   Boyd et al.
5,843,882 A   12/1998   Boyd et al.
5,962,653 A   10/1999   Boyd et al.
6,015,876 A    1/2000   Boyd
6,193,982 B1   2/2001   Boyd

FOREIGN PATENT DOCUMENTS

WO    WO 00/53213    9/2000

OTHER PUBLICATIONS

Mori T. Analysis of Sequence Requirements for Biological Activity of Cyanovirin-N, a Potent HIV-Inactivating Protein. Biochemical and Biophysical Research Communications 1997, vol. 238, p. 218-222.*
Han et al. Discovery of a Stable Dimeric Mutant of Cyanovirin-N (CV-N) from a T7 Phage-Displayed CV-N Mutant Library 2002, Biochemical and Biophysical Research Communications vol. 292, p. 1036-1043.*
Bergdoll et al., *Structure*, 5, 391-401 (1997).
Bewley, *J. Am. Chem. Soc.*, 123, 1014-1015 (2001).
Bewley et al., *J. Am. Chem. Soc.*, 123, 3892-3902 (2001).
Bewley et al., *J. Am. Chem. Soc.*, 122, 6009-6016 (2000).
Bewley et al., *Nat. Struct. Biol.*, 5(7), 571-578 (1998).
Bewley, *Structure*, 9, 931-940 (2001).
Boyd et al., *Antimicrob Agents Chemother.*, 41(7), 1521-1530 (1997).
Clore et al., *Biochem.*, 29, 7387-7401 (1990).
Dey et al., *J. Virol.*, 74(10), 4562-4569 (2000).
Morgan et al., *AIDS Res. Hum. Retroviruses*, 10(11), 1507-1515 (1994).
Tjandra et al., *J. Biomol. NMR*, 8, 273-284 (1996).
Yang et al., *J. Mol. Biol.*, 288, 403-412 (1999).
Barrientos et al., *PROTEINS: Structure, Function, and Genetics*, 46, 153-160 (2002).
Barrientos et al., *Structure*, 10, 673-686 (2002).
Kelley et al., *J. Am. Chem. Soc.*, 124, 3210-3211 (2002).

* cited by examiner

*Primary Examiner*—Jeffrey S. Parkin
*Assistant Examiner*—Louise Humphrey
(74) *Attorney, Agent, or Firm*—Leydig, Voit & Mayer, Ltd.

(57) ABSTRACT

The present invention relates to a purified or isolated obligate domain-swapped dimer of CVN and a composition comprising the same.

6 Claims, No Drawings

SEQUENCE LISTING

<160> NUMBER OF SEQ ID NOS: 2

<210> SEQ ID NO 1
<211> LENGTH: 39
<212> TYPE: DNA
<213> ORGANISM: Artificial Sequence
<220> FEATURE:
<223> OTHER INFORMATION: Synthetic

<400> SEQUENCE: 1
gacggttccc tgaaatggcc gtccaacttc atcgaaacc                              39

<210> SEQ ID NO 2
<211> LENGTH: 39
<212> TYPE: DNA
<213> ORGANISM: Artificial Sequence
<220> FEATURE:
<223> OTHER INFORMATION: Synthetic

<400> SEQUENCE: 2
ggtttcgatg aagttggacg gccatttcag ggaaccgtc                              39

OBLIGATE DOMAIN-SWAPPED DIMER OF CYANOVIRIN WITH ENHANCED ANTI-VIRAL ACTIVITY

CROSS-REFERENCE TO RELATED PATENT APPLICATIONS

This application is the U.S. national phase of International Patent Application No. PCT/US03/06115, which was filed on Feb. 25, 2003, and which claims the benefit of U.S. Provisional Patent Application No. 60/359,360, which was filed on Feb. 25, 2002.

TECHNICAL FIELD OF THE INVENTION

The present invention relates to an obligate domain-swapped dimer of cyanovirin (CVN); a nucleic acid encoding same, optionally in the form of a vector; a host cell comprising such a nucleic acid; a composition comprising (i) the obligate domain-swapped dimer of CVN or the nucleic acid encoding same, optionally in the form of a vector, and (ii) a carrier therefor; a method of inhibiting a viral infection of a mammal by administering to the mammal an antiviral effective amount of the aforementioned composition; and a method of making an obligate domain-swapped dimer of CVN by introducing at least one mutation in the linker region of wild-type CVN.

BACKGROUND OF THE INVENTION

CVN, a protein isolated from cyanobacteria, is known to have anti-viral activity. By interfering with the interaction of the viral envelope glycoprotein gp120 of human immunodeficiency viruses (HIV) with the surface of a cell, CVN can block the entry of HIV into the cell at nanomolar concentrations (Boyd et al., Animicrob. Agents Chemother. 41: 1521-1530(1997); Dey et al., J. Virol. 74: 4562-4569 (2000)). CVN:gp120 interactions are governed by high affinity binding of CVN to the D1 and D3 arms of oligomannose-8 and oligomannose-9, two oligosaccharides that are abundant on the surface of HIV (Bewley et al., J. Am. Chem. Soc. 123: 3892-3902 (2001)). This unprecedented specificity arises from the presence of two extensive carbohydrate binding pockets that are specific for the disaccharide oligomannose-α (1-2) oligomannose-α, i.e., the termini of the more accessible D1 and D3 arms of oligomannose-8 and oligomannose-9 (Bewley, Structure 9: 931-940 (2001)).

It is an object of the present invention to enhance the anti-viral activity of CVN. This and other objects and advantages of the present invention, as well as additional inventive features, will become apparent from the detailed description provided herein.

BRIEF SUMMARY OF THE INVENTION

The present invention provides a purified or isolated obligate domain-swapped dimer of CVN. Also provided are an isolated or purified nucleic acid encoding at least one obligate domain-swapped dimer of CVN, optionally in the form of a vector, and a host cell comprising such an isolated or purified nucleic acid. A composition comprising (i) the obligate domain-swapped dimer of CVN or the isolated or purified nucleic acid encoding at least one obligate domain-swapped dimer of CVN, optionally in the form of a vector, and (ii) a carrier therefor is also provided.

Accordingly, a method of inhibiting a viral infection of a mammal is also provided. The method comprises administering to the mammal an antiviral effective amount of the aforementioned composition, whereupon the viral infection of the mammal is inhibited.

A method of making an obligate domain-swapped dimer of CVN is also provided. The method comprises introducing at least one mutation in the linker region of wild-type CVN, whereupon an obligate domain-swapped dimer of CVN is obtained.

DETAILED DESCRIPTION OF THE INVENTION

The present invention is predicated, at least in part, on the discovery that an obligate domain-swapped dimer of CVN has enhanced antiviral activity. Accordingly, the present invention provides a purified or isolated obligate domain-swapped dimer of cyanovirin. By "cyanovirin" is meant the isolated and purified native antiviral protein referred to as cyanovirin-N and obtained from *Nostoc ellipsosporum* as well as any related, functionally equivalent protein, peptide or derivative thereof. Desirably, the overall length of the linker region of CVN and the orientation of the two domains of CVN relative to each other are changed, such that the torsion angles are changed and a rigid structure is imposed. Preferably, the dimer is a tetravalent carbohydrate binding protein, which preferably is stable at a pH from about 2.3 to about 8.0. Preferably, the dimer comprises the amino acid sequence of wild-type CVN in which there is at least one mutation in the linker region. Preferably, the at least one mutation is in the region from about amino acid position 48 to about amino acid position 54. In a preferred embodiment of the dimer, the glutamine at amino acid position 50 of CVN is deleted. Alternatively, a proline is inserted in the region from about amino acid position 50 to about amino acid position 53 or an amino acid in the region from about amino acid position 50 to about amino acid position 53 is substituted with a proline.

Cyanovirin (CVN) can be isolated from *N. ellipsosporum* in accordance with methods known in the art. See, e.g., U.S. Pat. No. 5,962,653. Alternately, the polypeptide can be synthesized using standard peptide synthesizing techniques well-known to those of skill in the art (e.g., as summarized in Bodanszky, Principles of Peptide Synthesis (Springer-Verlag, Heidelberg: 1984)). In particular, the polypeptide can be synthesized using the procedure of solid-phase synthesis (see, e.g., Merrifield, J. Am. Chem. Soc. 85: 2149-54 (1963); Barany et al., Int. J. Peptide Protein Res. 30: 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The polypeptide-containing mixture then can be extracted, for instance, with dimethyl ether, to remove non-peptidic organic compounds, and the synthesized polypeptide can be extracted from the resin powder (e.g., with about 25% w/v acetic acid). Following the synthesis of the polypeptide, further purification (e.g., using high performance liquid chromatography (HPLC)) optionally can be done in order to eliminate any incomplete polypeptides or free amino acids. Amino acid and/or HPLC analysis can be performed on the synthesized polypeptide to validate its identity.

Since the nucleotide and corresponding amino acid sequences of cyanovirin are known (see, e.g., SEQ ID NOS: 1 and 2, respectively, in U.S. Pat. No. 5,843,882), cyanovirin also can be recombinantly produced or synthesized in accordance with methods known in the art. See, e.g., U.S. Pat. Nos. 5,821,081 and 5,843,882 and the references cited under "Examples."

An obligate domain-swapped dimer of CVN can be made in accordance with methods known in the art. In this regard, mutations, such as insertions, deletions, substitutions and/or inversions, can be introduced in the linker region at the amino acid level or at the nucleic acid level. For instance, site-specific mutations can be introduced by ligating into an expression vector a synthesized oligonucleotide comprising the modified site. Alternately, oligonucleotide-directed site-specific mutagenesis procedures can be used, such as disclosed in Walder et al., Gene 42: 133 (1986); Bauer et al., Gene 37: 73 (1985); Craik, Biotechniques: 12-19 (January 1995); U.S. Pat. Nos. 4,518,584 and 4,737,462; Carter et al., Nucl. Acids Res. 13: 4331 (1986); and Zoller et al., Nucl. Acids Res. 10: 6487 (1987)), cassette mutagenesis (Wells et al., Gene 34: 315 (1985)), restriction selection mutagenesis (Wells et al., Philos. Trans. R. Soc. London SerA 317: 415 (1986)) and DNA synthesis of the mutated CVN. A preferred means for introducing mutations is the QuikChange Site-Directed Mutagenesis Kit (Stratagene, LaJolla, Calif.). When modifying the nucleic acid so that a new amino acid is substituted for that which is naturally occurring, the codon encoding the amino acid sequence to be substituted may be any of the alternative codons known to code for the particular amino acid (see, e.g. Lewin GENES V Oxford University Press, page 172 (1994)).

The dimer can be optionally glycosylated, amidated, carboxylated, phosphorylated, esterified, N-acylated or converted into an acid addition salt. Methods of protein modification (e.g., glycosylation, amidation, carboxylation, phosphorylation, esterification, N-acylation, and conversion into acid addition salts) are known in the art. Preferably, the dimer is not glycosylated.

The anti-viral, e.g., anti-HIV, activity of the dimer can be assessed in accordance with the assay set forth in Example 2 or in a series of interrelated in vitro antiviral assays (Gulakowski et al., J. Virol. Methods 33: 87-100 (1991)), which accurately predict for antiviral activity in humans. These assays measure the ability of compounds to prevent the replication of HIV and/or the cytopathic effects of HIV on human target cells. These measurements directly correlate with the pathogenesis of HIV-induced disease in vivo.

Fusion proteins comprising at least one dimer and conjugates comprising at least one dimer also can be generated. Such fusion proteins and conjugates can be generated in accordance with the methods of U.S. Pat. Nos. 5,962,688 and 6,245,737 as well as International Patent Application No. WO 00/53213.

An isolated or purified nucleic acid encoding at least one obligate domain-swapped dimer of CVN, optionally in the form of a vector, is also provided. The nucleic acid molecule can be cloned into any suitable vector and can be used to transform or transfect any suitable host. The selection of vectors and methods to construct them are commonly known to persons of ordinary skill in the art and are described in general technical references (see, in general, "Recombinant DNA Part D," Methods in Enzymology, Vol. 153, Wu and Grossman, eds., Academic Press (1987) and the references cited herein under "Examples"). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host. In this regard, the vector can encode two, three, four, five, six, seven and even eight of the obligate domain-swapped dimers of CVN, which can be the same or different.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE 1, 2 mμ plasmid, λ, SV40, bovine papilloma virus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. A preferred cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI101, pBI101.2, pBI101.3, pBI121 and pBIN19 (Clontech). Examples of animal expression vectors include pEUK-Cl, pMAM and pMAMneo (Clontech).

An expression vector can comprise a native or normative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule as described above with a promoter is also within the skill in the art.

Optionally, the isolated or purified nucleic acid molecule, upon linkage with another nucleic acid molecule, can encode a fusion protein. The generation of fusion proteins is within the ordinary skill in the art (see, e.g., references cited under "Example") and can involve the use of restriction enzyme or recombinational cloning techniques (see, e.g., Gateway™ (Invitrogen, Carlsbad, Calif.)). See, also, U.S. Pat. Nos. 5,314,995 and 5,962,688 and International Patent Application No. WO 00/53213.

Also in view of the above, the present invention provides a host cell comprising and expressing an above-described isolated or purified nucleic acid molecule, optionally in the form of a vector, as described above. Examples of host cells include, but are not limited to, bacteria, such as species within the genera *Escherichia* (e.g., *E. coli* TB-1, TG-2, DH5α, XL-Blue MRF' (Stratagene), SA2821 and Y1090), *Bacillus* (e.g., *B. subtilis*), *Pseudomonas* (e.g., *P. aerugenosa*), and *Salmonella*, as well as *lactobacilli*, yeast, such as *S. cerevisiae* or *N. crassa*, insect cells (e.g., Sf9, Ea4 and baculoviral systems (e.g., as described by Luckow et al., Bio/Technology 6: 47 (1988)), mammalian cells, including human cells, and established cell lines, such as the COS-7, C127, 3T3, CHO, HeLa, and BHK cell lines, and the like. The ordinarily skilled artisan is, of course, aware that the choice of expression host has ramifications for the type of polypeptide produced. For instance, the glycosylation of polypeptides produced in yeast or mammalian cells (e.g., COS-7 cells) will differ from that of polypeptides produced in bacterial cells, such as *E. coli*.

The present invention also provides a composition comprising (i) either of an above-described dimer or nucleic acid, optionally in the form of a vector, and (ii) a carrier therefore. Suitable carriers, such as pharmaceutically acceptable carriers, are well-known in the art, and are readily available. The choice of carrier will be determined in part by the particular route of administration and whether a nucleic acid molecule or dimer is being administered. Accordingly, there is a wide variety of suitable formulations for use in the context of the present invention, and the present invention expressly provides a pharmaceutical composition that comprises an active agent of the invention and a pharmaceutically acceptable carrier therefor. The following methods and carriers are merely exemplary and are in no way limiting.

Formulations suitable for oral administration can consist of (a) liquid solutions, such as an effective amount of the active agent dissolved in diluent, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth. Pastilles can comprise the active ingredient in an inert base, such as gelatin and glycerin, or sucrose and acacia, emulsions, gels, and the like containing, in addition to the active ingredient, such excipients/carriers as are known in the art.

An active agent of the present invention, either alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, active agents of the present invention can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate. Further suitable formulations are found in Remington's Pharmaceutical Sciences, 17th ed., (Mack Publishing Company, Philadelphia, Pa.: 1985), and methods of drug delivery are reviewed in, for example, Langer, Science 249: 1527-1533 (1990). Similarly, the active ingredient can be combined with a lubricant as a coating on a condom. Indeed, preferably, the active ingredient is applied to any contraceptive device, including, but not limited to, a condom, a diaphragm, a cervical cap, a vaginal ring, and a sponge. Such formulations allow for vaginal, rectal, penile or other topical routes of administration in the inhibition of viral infection through sexual activity. In this regard, *lactobacilli*, which express the dimer, can be introduced into the vagina.

Formulations for rectal administration can be presented as a suppository with a suitable base comprising, for example, cocoa butter or a salicylate.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

In the event that it becomes desirable or necessary to enhance further the stability of the dimer, such methods are known in the art. See, e.g., International Patent Application No. WO 00/53213.

The above compositions can contain other active agents, such as those which inhibit viral infection. Representative examples of these additional active agents include antiviral compounds, virucides, immunomodulators, immunostimulants, antibiotics and absorption enhancers. Exemplary antiviral compounds include AZT, ddI, ddC, gancylclovir, fluorinated dideoxynucleosides, normucleoside analog compounds, such as nevirapine (Shih et al., *PNAS* 88: 9878-9882 (1991)), TIBO derivatives, such as R82913 (White et al., *Antiviral Res.* 16: 257-266 (1991)), BI-RJ-70 (Merigan, *Am. J. Med.* 90 (Suppl.4A): 8S-17S (1991)), michellamines (Boyd et al., *J. Med. Chem.* 37: 1740-1745 (1994)) and calanolides (Kashman et al., *J. Med. Chem.* 35: 2735-2743 (1992)), nonoxynol-9, gossypol and derivatives, and gramicidin (Bourinbair et al., *Life Sci./Pharmocol. Lett.* 54: PL5-9 (1994); and Bourinbair et al., *Contraception* 49: 131-137 (1994)). Exemplary immunomodulators and immunostimulants include various interleukins, sCD4, cytokines, antibody preparations, blood transfusions, and cell transfusions. Exemplary antibiotics include antifingal agents, antibacterial agents, and anti-*Pneumocystilis carnii* agents. Exemplary absorption enhancers include bile salts and other surfactants, saponins, cyclodextrins, and phospholipids (Davis, *Pharm. Pharmacol.* 44 (Suppl. 1): 186-190 (1992)).

In view of the above, the present invention also provides a method of inhibiting a viral infection in a mammal. The method comprises administering to the mammal an antiviral effective amount of an above-described dimer, nucleic acid, optionally in the form of a vector, or composition comprising same, whereupon the viral infection of the mammal is inhibited. Preferably, the mammal is a human and the viral infection is human immunodeficiency viral infection.

The dimers can be used to inhibit a virus, specifically a retrovirus, more specifically an immunodeficiency virus, such as the human immunodeficiency virus, i.e., HIV-1 or HIV-2. The dimers also can be used to inhibit other retroviruses as well as other viruses. Examples of viruses that may be inhibited in accordance with the present invention include, but are not limited to, Type C and Type D retroviruses, HTLV-1, HTLV-2, HIV, FIV, FLV, SIV, MLV, BLV, BIV, equine infectious virus, anemia virus, avian sarcoma viruses, such as Rous sarcoma virus (RSV), hepatitis type A, B, non-A and non-B viruses, arboviruses, varicella viruses, human herpes virus (e.g., HHV-6), measles, mumps, influenza, and rubella viruses.

Generally, when an above-described dimer is administered to an animal, such as a mammal, in particular a human, such as in accordance with any of the methods set forth in International Patent Application No. WO 00/53213, it is preferable that the dimer is administered in a dose of from about 1 to about 1,000 micrograms of the dimer per kg of the body weight of the host per day when given parenterally.

However, this dosage range is merely preferred, and higher or lower doses can be chosen in appropriate circumstances. For instance, the actual dose and schedule can vary depending on whether the composition is administered in combination with other pharmaceutical compositions, or depending on interindividual differences in pharmacokinetics, drug disposition, and metabolism. One skilled in the art easily can make any necessary adjustments in accordance with the necessities of the particular situation.

Those of ordinary skill in the art can easily make a determination of the amount of an above-described isolated and purified nucleic acid molecule, which is optionally in the form of a vector, to be administered to an animal, such as a mammal, in particular a human. The dosage will depend upon the particular method of administration, including any vector or promoter utilized. For purposes of considering the dose in terms of particle units (pu), also referred to as viral particles, it can be assumed that there are 100 particles/pfu (e.g., $1 \times 10^{12}$ pfu is equivalent to $1 \times 10^{14}$ pu). An amount of recombinant virus, recombinant DNA vector or RNA genome sufficient to achieve a tissue concentration of about $10^2$ to about $10^{12}$ particles per ml is preferred, especially of about $10^6$ to about $10^{10}$ particles per ml. In certain applications, multiple daily doses are preferred. Moreover, the number of doses will vary, depending on the means of delivery and the particular vector administered.

Administration of a dimer with other anti-retroviral agents and particularly with known RT inhibitors, such as ddC, AZT, ddI, ddA, or other inhibitors that act against other HIV proteins, such as anti-TAT agents, is expected to inhibit most or all replicative stages of the viral life cycle. The dosages of ddC and AZT used in AIDS or ARC patients have been published. A virustatic range of ddC is generally between 0.05 µM to 1.0 μM. A range of about 0.005-0.25 mg/kg body weight is virustatic in most patients. The preliminary dose ranges for oral administration are somewhat broader, for example 0.001 to 0.25 mg/kg given in one or more doses at intervals of 2, 4, 6, 8, 12; etc. hours. Currently, 0.01 mg/kg body weight ddC given every 8 hrs is preferred. When given in combined therapy, the other antiviral compound, for example, can be given at the same time as the dimer or the dosing can be staggered as desired. The two drugs also can be combined in a composition. Doses of each can be less when used in combination than when either is used alone.

It will also be appreciated by one skilled in the art that a DNA sequence of a cyanovirin or conjugate thereof of the present invention can be inserted ex vivo into mammalian cells previously removed from a given animal, in particular a human, host. Such cells can be employed to express the dimer in vivo after reintroduction into the host. Feasibility of such a therapeutic strategy to deliver a therapeutic amount of an agent in close proximity to the desired target cells and pathogens, i.e., virus, more particularly retrovirus, specifically HIV and its envelope glycoprotein gp120, has been demonstrated in studies with cells engineered ex vivo to express sCD4 (Morgan et al., AIDS Res. Hum. Retrovir. 10: 1507-1515 (1994)). It is also possible that, as an alternative to ex vivo insertion of the DNA sequences of the present invention, such sequences can be inserted into cells directly in vivo, such as by use of an appropriate viral vector. Such cells transfected in vivo are expected to produce viral-inhibiting amounts of dimer directly in vivo.

Given the present disclosure, it will be additionally appreciated that a nucleic acid encoding a dimer can be inserted into suitable nonmammalian host cells, and that such host cells will express the dimer directly in vivo within a desired body compartment of an animal, in particular a human, in an amount sufficient to inhibit viral infection.

In a preferred embodiment of the present invention, a method of female-controllable prophylaxis against viral infection comprises the intravaginal administration and/or establishment of, in a female human, a persistent intravaginal population of *lactobacilli* that have been transformed with a dimer-encoding sequence to produce, over a prolonged time, levels of the dimer, directly on or within the vaginal and/or cervical and/or uterine mucosa, sufficient to inhibit viral infection.

The dimer, whether in the form of a protein or nucleic acid encoding same as described above, can be used in other methods. See, e.g., U.S. Pat. No. 6,015,876 and International Patent Application No. WO 00/53213. The dimer (or conjugate or fusion protein thereof) also can be used to remove virus from a sample as described in WO 00/53213.

A method of making an obligate domain-swapped dimer of CVN is also provided. The method comprises introducing at least one mutation in the linker region of wild-type CVN, whereupon an obligate domain-swapped dimer of CVN is obtained. The mutations can be introduced at the nucleic acid or amino acid level in accordance with methods known in the art as discussed above. Preferably, the at least one mutation is in the region from about amino acid position 48 to about amino acid position 54. Preferably, glutamine at amino acid position 50 is deleted. Alternatively, a proline is inserted in the region from about amino acid position 50 to about amino acid position 53 or an amino acid in the region from about amino acid position 50 to about amino acid position 53 is substituted with a proline.

EXAMPLES

The following examples serve to illustrate the present invention and are not intended to limit its scope in any way.

The following references, to the extent that they provide exemplary procedural or other details supplementary to those set forth herein, are specifically incorporated herein by reference:

Birren et al., Genome Analysis: A Laboratory Manual Series, Volume 1, Analyzing DNA, Cold Spring Harbor Laboratory Press, Cold Spring Harbor, N.Y. (1997), Birren et al., Genome Analysis: A Laboratory Manual Series, Volume 2, Detecting Genes, Cold Spring Harbor Laboratory Press, Cold Spring Harbor, N.Y. (1998), Birren et al., Genome Analysis: A Laboratory Manual Series, Volume 3, Cloning Systems, Cold Spring Harbor Laboratory Press, Cold Spring Harbor, N.Y. (1999), Birren et al., Genome Analysis: A Laboratory Manual Series, Volume 4, Mapping Genomes, Cold Spring Harbor Laboratory Press, Cold Spring Harbor, N.Y. (1999), Harlow et al., Antibodies: A Laboratory Manual, Cold Spring Harbor Laboratory Press, Cold Spring Harbor, N.Y. (1988), Harlow et al., Using Antibodies: A Laboratory Manual, Cold Spring Harbor Laboratory Press, Cold Spring Harbor, N.Y. (1999), and Sambrook et al., Molecular Cloning: A Laboratory Manual, 2nd edition, Cold Spring Harbor Laboratory Press, Cold Spring Harbor, N.Y. (1989).

Nuclear magnetic resonance (NMR) spectra were recorded on a Bruker DMX500 MHz spectrometer equipped with x,y,z-shielded gradient triple resonance probes. Analytical ultracentrifugation experiments were conducted at 20.0° C. on a Beckman Optima XL-A analytical ultracentrifuge. Protein samples were prepared in 20 mM sodium phosphate buffer, pH 6.4, and loaded into the ultracentrifuge cells at loading concentrations of 20 μM. Data were analyzed in terms of a single ideal solute to obtain the buoyant molecular mass, M(1-vρ), using the Optima XL-A data analysis software (Beckman). The value for the experimen tal molecular mass, M, was determined using calculated values for the density, ρ (determined at 20.0° C. using standard tables), and partial specific volume, v (calculated on the basis of amino acid composition). Site-directed mutagenesis on a pet46A plasmid containing a synthetic gene encoding wild-type CVN was performed using the Stratagene (La Jolla, Calif.) QuikChange™ Kit according to the manufacturer's instructions. Forward and reverse primers with respective sequences of 5'-GACGGTTCCCT-GAAATGGCCGTCCAACTTCATCGAAACC-3' [SEQ ID NO: 1] and 5'-GGTTTCGATGAAGTTGGACGGC-CATTTCAGGGAACCGTC-3' [SEQ ID NO: 2] were used for the PCR reactions, and were gel-purified before use (Lofstrand Labs, Gaithersburg, Md.). DNA sequencing of the deletion mutant insert was performed on an ABI PRISM DNA sequencer (Applied Biosystems) on polymerase chain reaction (PCR) products generated with Rhodamine Terminator (Perkin Elmer) labeling of the sequence between the T7 promoter and terminator, according to the manufacturer's instructions. Reversed-phase high pressure liquid chromatography (HPLC) was carried out on a GBC HPLC system using a YMC ODS 18 25 mm×25 cm column, eluting with a gradient of 20%-40% $CH_3CN$ in aqueous TFA over 45 minutes, with a flow rate of 6 ml/min. Gel filtration was carried out on a AKTA FPLC using a Superdex75 10/30 analytical gel filtration column (Amersham-Pharmacia Biotech), equilibrated and eluted with 20 mM $NaPO_4$, pH 6.4, at a flow rate of 0.5 ml/min.

Example 1

This example demonstrates the production of an obligate domain-swapped dimer of CVN.

CVN has a pseudosymmetrical, three-dimensional structure comprising two adjacent triple-stranded anti-parallel β-sheets in the back of the protein and two oppositely placed β-hairpins on the front of the protein, each of which is preceded by a single 310 helical turn (Bewley et al., Nature Struct. Biol. 5: 571-578 (1998)). The homologous sequence repeats (residues 1-50 and 51-101) are separated by a central linker (comprising Gln50-Pro51-Ser52-Asn53) that precisely crosses over β-strand 4 (Bewley et al. (1998), supra) and facilitates domain swapping (Yang et al., J. Mol. Biol. 288: 403-412 (1999)). Since the presence of proline in hinge linkers correlates with domain-swapping (Bergdoll et al., Structure 5: 391-401 (1997)) and Ser52 and Asn53 participate in carbohydrate binding (Bewley (2001), supra), Gln50 was selected for deletion from the linker so as to generate an obligate dimer.

The CVN Gln50 deletion mutant (ΔQ50-CVN) was constructed by site-directed mutagenesis and uniformly labeled $^{15}N$-ΔQ50-CVN was overexpressed as described previously (Bewley et al. (1998), supra). The recombinant protein was purified from a crude cell lysate (50% aqueous $CH_3CN$) in a single step by reversed-phase HPLC. The presence and relative abundance of monomeric and dimeric wild-type CVN can be readily assessed from a $^1H$-$^{15}N$ HSQC single quantum coherence correlation spectrum (HSQC), which shows doubling of 18 resolved signals (Bewley et al., J. Am. Chem. Soc. 122: 6009-6016 (2000)). $^1H$-$^{15}N$ HSQC spectra of NMR samples of ΔQ50-CVN (10% $D_2O$) prepared with and without adjusting the pH (measured pH values of 6.4 and 2.3, respectively) were recorded. Unlike wild-type CVN, which shows the presence of approximately 25% domain-swapped dimer upon dissolution (pH approx. 2.3-3.0), the $^1H$-$^{15}N$ HSQC spectrum of ΔQ50-CVN revealed the presence of a single species, regardless of pH. NMR relaxation measurements were carried out to determine whether this single species was monomeric or dimeric. At 35° C., samples of ΔQ50-CVN had average $^1H_N$ and $^{15}N$ $T_2$ values (Tjandra et al., J. Biomol. NMR 8: 273-284 (1996)) of 22 ms and 93 ms, respectively, and a rotational correlation time (Clore et al., Biochem. 29: 7387-7401 (1990)) τc of 9.7 ns (Table 1), values that are only consistent with a dimer of approx. 22 kDa. In addition, equilibrium sedimentation measurements for ΔQ50-CVN yielded an average molecular mass of 24 (+0.9) kDa, further confirming that ΔQ50-CVN is an obligate dimer.

TABLE 1

| | Relaxation Parameters | | |
|---|---|---|---|
| Protein | 1HNT2 a | 15NT2 a | τc b |
| ΔQ50-CVN | ~22 ms | 93 + 4 ms | 9.7 ns |
| Dimeric CVN | ~20 ms | 95 + 6 ms | 9.6 ns |
| Monomeric CVN | ~40 ms | 167 + 14 ms | 4.5 ns | a $^1H_N$ $T_2$ and $^{15}N$ $T_2$ values were measured as described in Tjandra et al. (1996), supra.
b τc values were calculated from $^{15}N$ $T_1/T_2$ ratios as described in Clore et al. (1990), supra.

Example 2

This example demonstrates that an obligate domain-swapped dimer of CVN has enhanced antiviral activity compared to wild-type CVN.

CVN potently inhibits entry into a cell by HIV (Boyd et al., (1997), supra; Dey et al. (2000), supra; and Bewley et al. (2001), supra). In order to determine the comparative efficacy of ΔQ50-CVN, ΔQ50-CVN, dimeric wild-type CVN, and monomeric wild-type CVN (obtained after gel filtration chromatography) were tested in parallel in a quantitative vaccinia virus-based HIV-1 fusion assay (Nussbaum et al., J. Virol. 68: 5411-5422 (1994)). ΔQ50-CVN and dimeric wild-type CVN were more potent inhibitors of HIV-1 fusion than monomeric wild-type CVN. Non-linear least squares best fitting of the titration data to a two-independent site model (Bewley et al. (2001), supra) for ΔQ50-CVN, dimeric wild-type CVN, and monomeric wild-type CVN yielded average KDs of 22 nM, 21 nM and 67 nM, respectively, with corresponding $IC_{50}$ values of 9 nM, 9 nM and 32 nM. Thus, an obligate domain-swapped dimer of CVN has enhanced antiviral activity compared to monomeric wild-type CVN.

All of the references cited herein, including journal articles, patents, patent applications, and publications, are hereby incorporated in their entireties by reference.

While this invention has been described with an emphasis upon preferred embodiments, variations of the preferred embodiments can be used, and it is intended that the invention can be practiced otherwise than as specifically described herein. Accordingly; this invention includes all modifications encompassed within the spirit and scope of the invention as defined by the claims.

What is claimed is:

1. A purified obligate domain-swapped mutant dimer of cynaovirin (CVN) comprising a Gln50 deletion (ΔQ50-CVN), wherein said mutant has enhanced antiviral activity as compared to wild type CVN.

2. The purified obligate domain-swapped dimer of CVN of claim 1, which is a tetravalent carbohydrate-binding protein.

3. The purified obligate domain-swapped dimer of CVN of claim 2, which is stable at a pH from about 2.3 to about 8.0.

4. A composition comprising the obligate domain-swapped dimer of CVN of claim 1 and a carrier.

5. A composition comprising the obligate domain-swapped dimer of CVN of claim 2 and a carrier.

6. A composition comprising the obligate domain-swapped dimer of CVN of claim 3 and a carrier.

* * * * *